United States Patent [19]

Ashby et al.

[11] 4,288,345

[45] Sep. 8, 1981

[54] PLATINUM COMPLEX

[75] Inventors: Bruce A. Ashby, Schenectady; Frank J. Modic, Scotia, both of N.Y.

[73] Assignee: General Electric Company, Waterford, N.Y.

[21] Appl. No.: 119,014

[22] Filed: Feb. 6, 1980

[51] Int. Cl.$^3$ .................. C07F 15/00; B01J 31/12
[52] U.S. Cl. .................. 252/431 R; 260/429 R; 528/15; 528/31; 528/32
[58] Field of Search .............. 260/429 R; 252/431 R; 528/15, 31, 32

[56] References Cited

U.S. PATENT DOCUMENTS

| | | | |
|---|---|---|---|
| 3,159,601 | 12/1964 | Ashby | 260/429 R X |
| 3,159,662 | 12/1964 | Ashby | 260/429 R X |
| 3,324,157 | 6/1967 | Wilkus et al. | 260/429 R X |
| 3,383,356 | 5/1968 | Nielsen | 260/429 R X |
| 3,414,597 | 12/1968 | Wilkus et al. | 260/429 R |
| 3,419,593 | 12/1968 | Willing | 260/429 R |
| 3,453,234 | 7/1969 | Kookootsedes | 260/429 R X |
| 3,522,327 | 7/1970 | Parasko | 260/429 R X |
| 3,775,452 | 11/1973 | Karstedt | 252/431 R X |
| 3,795,656 | 3/1974 | Martin | 260/429 R X |

*Primary Examiner*—Helen M. S. Sneed
*Attorney, Agent, or Firm*—Morgan, Finnegan, Pine, Foley & Lee

[57] ABSTRACT

Platinum complexes of unsaturated siloxanes, substantially free of inorganic halogen and inhibitory compounds, provide superior hydrosilation catalysts when the unsaturated siloxane comprises, per gram-atom of platinum, (i) a combination of one mole of $(CH_2\!=\!CH)((R)_2Si)_2O$, and one mole of $(CH_2\!=\!CH)(R)_2SiOSi(R_2)OH$;
(ii) two moles of $(CH_2\!=\!CH)((R)_2Si)_2O$; or
(iii) a mixture of (i) and (ii), wherein R is free of aliphatic unsaturation and is selected from alkyl, cycloalkyl, and aryl groups.

10 Claims, No Drawings

PLATINUM COMPLEX

The present invention relates to novel compositions for catalyzing the reaction of hydrogen-bonded silanes or siloxanes with aliphatically unsaturated and/or hydroxyl-containing organic compounds, especially aliphatically unsaturated and/or hydroxyl-containing organopolysiloxane compounds.

BACKGROUND OF THE INVENTION

In Willing, U.S. Pat. No. 3,419,593, and in Karstedt, U.S. Pat. No. 3,775,452, are described complex catalysts comprised of platinum and unsaturated siloxanes, and their use in the so-called hydrosilation reaction between compounds containing silicon-bonded hydrogen and aliphatically unsaturated organic compounds, especially aliphatically unsaturated organopolysiloxane compounds. It is also known to use such catalysts in the reaction of organo silanol compounds with hydrogenosiloxanes to produce a new siloxane and hydrogen gas. Curable compositions useful as encapsulants for electronic components, and the like, comprise organopolysiloxanes having at least two aliphatically unsaturated groups or at least two silicon-bonded hydroxyl groups, a silicon hydride, and such platinum complex catalysts and these can be provided in foamable modifications, as well as filled modifications, containing e.g., from 10 to 300 parts of filler per 100 parts of organopolysiloxane. The disclosures of the above-mentioned patents are incorporated herein by reference, and the latter-mentioned ones as well.

The Willing patent describes, typically, the heating together of symmetrical divinyltetramethyldisiloxane in large excess with chloroplatinic acid then cooling, diluting with still more of the disiloxane, filtering and then washing with water to remove acidity. Adding trace amounts of this composition to a mixture of a polyhydrogenmethyl siloxane and a vinyl-terminated polydimethylsiloxane, followed by gentle heating produces a gel, indicating that the known reaction between the ≡Si and CH$_2$=CH- linkages has taken place.

Karstedt discloses that superior catalysts can be formed if pains are taken to remove all, or substantially all, of the inorganic halogen which is produced in the reaction between a platinum halide and an unsaturated siloxane. The use of a compound like sodium bicarbonate is specified to remove inorganic halogen before the platinum-siloxane complex is used as a catalyst.

In the present state of the art, catalysts prepared by the Willing method have been found to be somewhat less than satisfactory in terms of rate of cure, for example, due to the presence of detectable amounts of inorganic halides, and catalysts prepared by both the Willing and the Karstedt method are less than optimum because they contain numerous intermediate structures and they appear to be encumbered by inhibitory impurities. While both patents appear to recognize the need to remove undesirable materials, such as starting reactants, reaction by-products, etc., neither contemplates the presence, much less the need to avoid anticatalysts, i.e., the inhibitory impurities. See, for example, inhibitors as described in Nielsen, U.S. Pat. No. 3,383,356.

It has now been found that two types of olefinic siloxanes of a very specific nature can be used alone, or in combination, as complexes with platinum to produce superior catalysts, e.g., in the hydrosilation reactions of hydrogenosiloxanes with olefinically unsaturated and/or hydroxylated organic compounds and the hydrosilation reactions of hydrogensiloxanes with olefinically unsaturated and/or hydroxyl-substituted organosiloxanes. The olefinic siloxanes each are disiloxanes, one having one vinyldiorganosilyl group and one hydroxyldiorganosilyl group; and the second having two vinyldiorganosilyl end groups. It is essential that the complexes (i) be free of detectable inorganic halogen and (ii) be free of inhibitory impurities. These requirements can be met in either of two ways: (i) prepare the complex catalyst from a non-halogen-containing intermediate, e.g., the platinum bis-1,5-cyclooctadiene complex of Green et al., J. Chem. Soc., Chem-Comm. 1975, p. 3 and the respective disiloxane; or (ii) follow the procedure of the above-mentioned patents and isolate the complex catalyst free of halogen and inhibitory impurities by new techniques, such as preparative high pressure liquid chromatography. As will be seen hereinafter, the resulting complexes produce high cure rates and activity at low levels of platinum which are unattainable by following the teachings of the prior art.

DESCRIPTION OF THE INVENTION

According to the present invention there are provided platinum-siloxane catalysts, substantially free of inhibitory impurities and detectable inorganic halogen, and consisting essentially of (i) one gram-atom of chemically combined platinum and one mole each of an organosiloxane of the formula

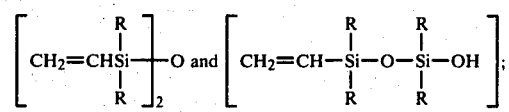

(ii) one gram-atom of chemically combined platinum and two moles of an organosiloxane of the formula

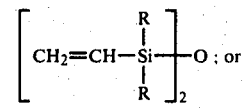

(iii) a combination of (i) and (ii); wherein R is free of aliphatic unsaturation and is selected from alkyl radicals, cycloalkyl radicals and phenyl radicals.

In preferred features, R is methyl, and, if (i) and (ii) are used in combination, then (i) will predominate, e.g., comprise greater than 50% by weight of the mixture (iii).

Also contemplated are compositions comprising (a) an organosilicon compound containing at least one ≡SiH bond;

(b) an organic compound containing an aliphatic unsaturated group, a hydroxyl group, or a mixture of such groups; and (c) a catalytic amount of a platinum-siloxane complex catalyst substantially free of inhibitory impurities and detectable inorganic halogen, and consisting essentially of (i) one gram-atom of chemically combined platinum and an organosiloxane combination of the formula

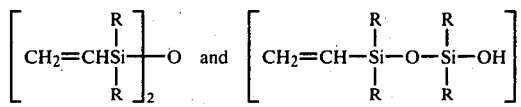

(ii) one gram-atom of chemically combined platinum and two moles of an organosiloxane of the formula

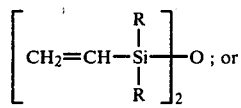

(iii) a combination of (i) and (ii); wherein R is free of aliphatic unsaturation and is selected from alkyl radicals, cycloalkyl radicals and phenyl radicals.

In preferred features, such compositions will be those in which component (a) is an organohydrogenpolysiloxane; component (b) is an organosilicon compound containing at least one silicon-bonded aliphatic unsaturated group, or an organosilicon compound containing at least one silicon-bonded hydroxyl group; and especially a vinyl-terminated polydimethylsiloxane or a hydroxy-terminated polydimethylsiloxane. In other preferred features, in the composition, in complex catalyst (c), R is methyl; and in said composition said complex catalyst (c) comprises predominately that defined under (i). Especially preferably said complex catalyst (c) consists essentially of that defined under (i) and wherein R is methyl.

The term "detectable inorganic halogen" will designate halogen that can be detected by a modification of ASTM designation D-1821-63 for "Inorganic Chloride". The procedure used is that set forth in the Karstedt patent above-mentioned. The modification comprises utilizing in place of acetone, which is the solvent specified in the test, a mixture of glacial acetic acid and acetone.

The term "substantially free of inhibitory impurities" means free of components which extend gel time at approximately room temperature, i.e., 25° C., more than 50% above that which is attainable with complexes comprising platinum and 100% of components designated (i), (ii) and (iii) above. A convenient way for determing such gel time is to make a master solution in a vinyl terminated or hydroxyl-terminated polydimethylsiloxane of the catalyst which will contain approximately 100 ppm. of platinum, dilute it to contain 10 ppm as Pt and then to mix this with a liquid organohydrogenpolysiloxane and to measure gel time. If the catalyst is substantially free of inhibitory impurities, it will exhibit a gel time of less than half that observed with the catalysts of the prior art.

The catalysts, as mentioned above, can be made by several procedures. In one manner of proceeding, bis-cyclooctadienyl platinum can be reacted with two moles of sym-divinyl tetraorgano disiloxane, during which two moles of 1,5-cyclooctadiene are split off. The products can be recovered by vacuum stripping the 1,5-cyclooctadiene, or by preparative liquid chromatography.

As in the above-mentioned patents, R can be alkyl, cycloalkyl, or aryl, illustratively containing from 1 to 18 carbon atoms, as the case may be, typically, methyl, ethyl, propyl, butyl, pentyl, hexyl, heptyl, octyl, etc., cyclohexyl, cycloheptyl, etc., phenyl, totyl, xylyl, etc. benzyl, phenylethyl, phenylpropyl, etc., If R is methyl, the products will be colorless liquids, sensitive to air and/or moisture and soluble in tetrahydrofuran, acetonitrile and hexane.

Alternatively, the catalysts can be prepared by reacting a platinum halide with the disiloxane under conditions in which inorganic halogen is removed, followed by isolation of the complex by methods leaving it substantially free of inhibiting impurities, as defined above. Suitable platinum halides are, for example, $H_2PtCl_6 \cdot nH_2O$, and metal salts such as $NaHPtCl_6 \cdot nH_2O$; $KHPtCl_6 nH_2O$; $Na_2PtCl_6 \cdot nH_2O$; $K_2PtCl_6 \cdot nH_2O$. Also $PtCl_4 \cdot nH_2O$ and platinous type halides such as $PtCl_2$; $Na_2PtCl_4 \cdot nH_2O$; $H_2PtCl_4 \cdot nH_2O$; $NaHPtCl_4 \cdot nH_2O$; $KHPtCl_4 \cdot nH_2O$; $K_3PtBr_4$, and the like. Furthermore, platinum halide complexes with aliphatic hydrocarbons as disclosed in Ashby U.S. Pat. No. 3,159,601 and 3,159,662 can be used, for example $[(CH_2=CH_2) \cdot PtCl_2]_2$; $(PtCl_2 \cdot C_2H_6)_2$; etc.

In a preferred procedure, an excess of sodium bicarbonate will be added to a mixture of chloroplatinic acid and divinyltetramethyldisiloxane in ethanol. The mixture is agitated and refluxed, then filtered and stripped of volatiles under vacuum. Then the residue is subjected to preparative liquid chromotagraphy to isolate the active components, substantially free of inhibitory compounds.

In addition to the above-described platinum-siloxane complexes, there are also included in the present invention, reactive compositions having at least 0.01 part, and preferably 1 to 200 parts of platinum per million parts of aliphatically unsaturated and/or hydroxyl-containing organic compound and a ≡SH containing material. In preferred compositions, the aliphatically unsaturated and/or hydroxyl-containing compound will be an organopolysiloxane, and especially preferably one of the compounds illustrated in this connection in Karstedt, U.S. Pat. No. 3,775,452. Such compositions are cured to the solid state with a variety of silicone hydrides, also as shown in Karstedt, U.S. Pat. No. 3,775,452. Suitable silicon hydrides are, for example, organocyclopolysiloxanes containing at least two chemically combined RHSiO units, and organopolysiloxane polymers having chemically combined (R)Si(H)O units, where R is as above defined. The organopolysiloxane can be a fluid having terminal diorganoalkenylsiloxy units, or terminal diorganohydroxysiloxy units such as dimethylvinylsiloxy units, having a viscosity of at least 50 centipoises at 25° C. In addition, organopolysiloxane gums having a viscosity of at least 100,000 centipoises at 25° C. and chemically combined methylvinylsiloxy and/or hydroxymethyl siloxy units, etc., can provide for elastomeric foaming products. In addition, the platinum containing orgaopolysiloxane of the present invention can contain from 10 to 300 parts of filler per 100 parts of organopolysiloxane. For example, fillers include, silica, such as fumed silica, non-reinforcing ground quartz, carbon black, and the like.

DESCRIPTION OF THE PREFERRED EMBODIMENTS

In order that those skilled in the art will be better able to practice the invention, the following examples are given by way of illustration and not by way of limitation. All parts are by weight.

EXAMPLE 1

Platinum Complex of 1,3-Divinyltetramethyldisiloxane.

A mixture of bis-cyclooctadienyl platinum (1 mole), prepared by the method of Green et al., J. Chem. Soc., Chem. Comm. 1975, page 3 and 1,3-divinyltetramethyldisiloxane (2 moles) is reacted in hexane, for 2 hrs. at 25° C. Then the reaction mixture is vacuum stripped at 25° C., 5 mm Hg. to remove 2 moles of 1,5-cyclooctadiene, leaving the desired catalytic complex product as a colorless liquid, soluble in tetrahydrofuran, acetonitrile and hexane.

EXAMPLE 2

There is added 20 parts of sodium bicarbonate to a mixture of 10 parts of $H_2PtCl_6 \cdot 6H_2O$, 20 parts of 1,3-divinyltetramethyldisiloxane and 50 parts of ethyl alcohol and the mixture is agitated while being refluxed for a period of 30 minutes, and left undisturbed for 15 hours (according to Karstedt, U.S. Pat. No. 3,775,452, Example 7). The preparation is stripped at 35° C. and 5 mm. Hg pressure to remove all solvent. The residue is examined with a Varian Model MAT-713 Field Desorption Mass Spectograph (FDMS) up to an M/e of about 788. The compounds containing platinum exhibit an array of isotope peaks characteristic of platinum. From the M/e of the compound, the most probable structure is assigned. As confirmation, the residue is separated into its components by high pressure liquid chromatography (HPLC). A chromatogram is developed using a Waters Model ALC-200 instrument with a gradient $CHCl_3$/hexane solvent system on a $\mu$-Bondapak CN column. The chromatogram exhibits two major components, A and B (in order of elution). The A/B peak ratio is 37/63. FDMS examination of peak A obtained by trapping appropriate volumes of eluate from multiple injections of the residue into the HPLC show it to correspond to the structure $[((CH_2=CH)(CH_3)_2Si)_2O]_2 \cdot Pt$, which corresponds also to Example 1, M/e 567. It is also noted that the observed intense isotope peak at 567 awu (atomic weight units) is the one predicted as the most intense from a computer modeling of the isotopic abundance of each element present in the structure set forth in the claims herein. In a like manner, peak B is shown to correspond to the structure, $[(CH_2=CH)(CH_3)_2Si]_2O \cdot (CH_2=CH)(CH_3)_2Si-O-Si(CH_3)_2(OH) \cdot Pt$ which has an intense isotope peak at 557 awu.

EXAMPLE 3

A mixture of 150 parts of distilled 1,3-divinyltetramethyldisiloxane and 3.2 g. of $H_2PtCl_6 \cdot 6H_2O$ is heated and stirred for 1 hr. at 120° C. (according to Willing, U.S. Pat. No. 3,419,593, Example 1). The volatiles are removed to 35° C. and 5 mm Hg. pressure and subjected to the combined analytical techniques, HPLC and FDMS, set forth in Example 2. The active substance present in most abundance corresponds to the formula, $Pt \cdot [(CH_2=CH)(CH_3)_2SiO(Si(CH_3)_2O)_xSi(CH_3)_2(CH=CH_2)] \cdot [(CH_2=CH)(CH_3)_2-SiO(Si(CH_3)_2O)_ySi(CH_3)_2(CH=CH_2)]$ wherein x and y are zero. There are also present appreciable amounts of compounds wherein x and y have finite values, in addition to zero. The compound wherein x and y are each zero (same as peak A in Example 2) is isolated by the method of Example 2 and is a catalyst according to this invention (the same as Example 1), even though it is initially present in lesser amount than the amount produced in Example 2.

EXAMPLES 4 and 5

In order to determine the activity of the catalysts of Example 1 (and 2 and 3) and to compare them with the catalysts of the prior art (Karstedt and Willing), samples of pure A and pure B as separated by HPLC by the procedure of Example 2 are obtained. The $CHCl_3$/hexane solvent is removed and replaced with sufficient pure hexane to give 0.2 weight percent (measured by X-ray fluorescence) platinum. Master solutions of these hexane solutions of A and B are prepared by adding them in an amount sufficient to provide 100 ppm Pt in a batch of 75 weight percent vinyl-terminated polydimethylsiloxane (3500 cps viscosity at 25° C.) and 25 weight percent of a soluble trimethyl, methylvinyl and $SiO_2$ units-containing organosiloxane copolymer. For comparison purposes, master solutions are prepared to contain 100 ppm platinum from Example 7, Karstedt, U.S. Pat. No. 3,775,452; and Example 1 of Willing, U.S. Pat. No. 3,419,593. The masters comprise:

Example 4 Compound A(Example 2) at 99.8 ppm.Pt.
Example 5 Compound B(Example 2) at 100.2 ppm Pt.
Comp. Example 4A Karstedt's Catalyst (Ex. 7) at 99.9 ppm. Pt.
Comp. Example 5A Willing's Catalyst (Ex. 1) at 100.3 ppm. Pt.

The masters are then used to prepare more dilute solutions in the same batch of 75:25 organopolysiloxane by combining 3 g. of each concentrated master and 27 g. of the polymer batch to give four final solutions, each containing 10 ppm. by weight of platinum. Next, there is added 3 g. of a 50:50 mixture of liquid organohydrogenpolysiloxane and the vinyl-terminated polydimethylsiloxane to the 30 g. solutions described above. The gel times at 25° C. are then measured with the following results:

| Test | Start | Gel |
| --- | --- | --- |
| Example 4 | Compound A | 10:19 A.M. | 3:20 P.M. |
| Example 5 | Compound B | 10:14 A.M. | 3:40 P.M. |
| Comp. Example 4A | Karstedt | 10:11 A.M. | 5:00 P.M. No Cure |
| Comp. Example 4B | Willing | 10:08 A.M. | 5:00 P.M. No Cure |

The next day, Test 4A was observed to gel at about 4:00 P.M. (30 hours); while test 4B did not gel until some time after 5:00 P.M. of that day and before 8:00 A.M. of the following (more than 31, but less than 46 hours). The excellent activity and freedom from inhibiting impurities of the complexes of Example 4 and 5 is thus demonstrated.

EXAMPLES 6 and 7

To further demonstrate the high efficiency of the catalyst compositions of the present invention, four foamable compositions are prepared. The foam formulation is:

I. 27 g. of an OH-terminated polydimethylsiloxane (31,500 cps viscosity at 25° C.)

II. 1.7 g. of a high silanol (7.3 wt.% H)-terminated polydimethyl siloxane

III. 3.0 g. of a methylhydrogenpolysiloxane containing 1.6 wt.% hydrogen (as H)

IV. 3.0 g. of the 100 ppm. Pt-containing masters of Examples 4, 5, 4A and 4B, as required.

The foregoing are combined by mixing I and IV to give 10 ppm. of Pt-containing solution. Then II is added and thoroughly mixed. Then III is added and a stop watch is used to determine the respective gel times at 25° C.

| Example | Catalyst | Gel time, sec. | Foam height (1-lowest 4-highest) |
|---|---|---|---|
| Ex. 6 | Compound A | 147 | 3 |
| Ex. 7 | Compound B | 120 | 4 |
| Comp. Ex. 6A | Karstedt | 480 | 2 |
| Comp. Ex. 7A | Willing | 860 | 1 |

The gel tests and the foam height measurements both indicate that the catalysts according to this invention are superior in terms of their freedom from inhibitory impurities.

Many variations will suggest themselves to those skilled in this art in light of the above, detailed description. All such obvious modifications are within the full intended scope of the appended claims.

We claim:

1. A platinum-siloxane complex catalyst, substantially free of inhibitory impurities and detectable inorganic halogen, and consisting essentially of
   (i) one gram-atom of chemically combined platinum and one mole each of an organosiloxane of the formula

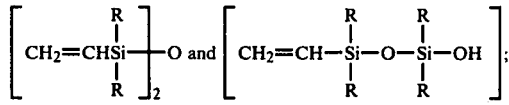

(ii) one gram-atom of chemically combined platinum and two moles of an organosiloxane of the formula

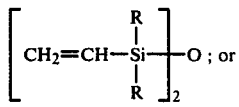

(iii) a combination of (i) and (ii); wherein R is free of aliphatic unsaturation and is selected from alkyl radicals, cycloalkyl radicals and phenyl radicals.

2. A complex catalyst as defined in claim 1 wherein R is methyl.

3. A complex catalyst as defined in claim 1 wherein, in said combination (iii), component (ii) comprises a minor proportion by weight.

4. A curable composition comprising
   (a) an organosilicon compound containing at least one ≡SiH bond;
   (b) an organic compound containing an aliphatic unsaturated group, a hydroxyl group, or a mixture of such groups; and
   (c) a catalytic amount of a platinum-siloxane complex catalyst substantially free of inhibitory impurities and detectable inorganic halogen, and consisting essentially of
   (i) one gram-atom of chemically combined platinum and one mole each of an organosiloxane of the formula

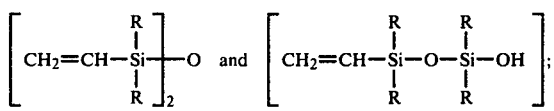

(ii) one gram-atom of chemically combined platinum and two moles of an organosiloxane of the formula

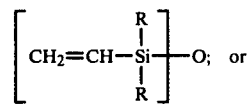

(iii) a combination of (i) and (ii);
   wherein R is free of aliphatic unsaturation and is selected from alkyl radicals, cycloalkyl radicals and phenyl radicals.

5. A composition as defined in claim 4 wherein component (a) is an organohydrogenpolysiloxane.

6. A composition as defined in claim 4 wherein component (b) is an organosilicon compound containing at least one silicon-bonded aliphatic unsaturated group, or an organosilicon compound containing at least one silicon-bonded hydroxyl group.

7. A composition as defined in claim 6 wherein said component (b) comprises a vinyl-terminated polydimethylsiloxane or a hydroxy-terminated polydimethylsiloxane.

8. A composition as defined in claim 4 wherein, in said complex catalyst (c), R is methyl.

9. A composition as defined in claim 4 wherein said complex catalyst (c) comprises predominantly that defined under (i).

10. A composition as defined in claim 4 wherein said complex catalyst (c) consists essentially of that defined under (i) and wherein R is methyl.

* * * * *